United States Patent [19]

Parkinson

[11] Patent Number: 4,735,794

[45] Date of Patent: Apr. 5, 1988

[54] METHOD FOR DRYING BIOLOGICAL SPECIMENS

[75] Inventor: Martin C. Parkinson, Nyack, N.Y.

[73] Assignee: Ted Pella, Inc., Redding, Calif.

[21] Appl. No.: 925,301

[22] Filed: Oct. 31, 1986

[51] Int. Cl.4 .................... G01N 1/30; G01N 33/48
[52] U.S. Cl. ...................................................... 424/3
[58] Field of Search .................. 424/52, 3, 5; 62/514, 62/394

[56] References Cited

PUBLICATIONS

Frobisher, M., Hinsdill, R. D., Crabtree, K. T., and Goodheart, C. R., Fundamentals of Microbiology, (W. B. Saunders Co., Phil., London, Toronto, 1974), p. 280.
Lachman, L., Lieberman, H. A., Kanig, O. L., The Theory and Practice of Industrial Pharmacy, (Lea & Febiger, Phil. 1976), p. 523.
Boyde A., Maconnachie, E., Freon 113 Freeze-drying for Scanning Electron Microscopy, Scanning 2(3), 164–6, (1979), in: *Chem. Abstr.*
Gray, Peter, The Encycl. of Microscopy and Microtechnique, (Van Nostrand Reinhold Co., 1973), p. 31.

*Primary Examiner*—Albert T. Meyers
*Assistant Examiner*—Michael S. Wysor
*Attorney, Agent, or Firm*—Martin Parkinson

[57] ABSTRACT

A method for preparing biological specimens for the scanning electron microscope utilizes a select group of fluorocarbon solvents. Replacement of drying solvents with a fluorocarbon solvent, followed by direct sublimation, provides comparable results to critical point drying.

5 Claims, No Drawings

METHOD FOR DRYING BIOLOGICAL SPECIMENS

BACKGROUND OF THE INVENTION

This invention relates to the drying of biological specimens prior to microscopic examination, and in particular to biological specimen preparation for the scanning electron microscope.

Scanning electron microscopes utilize electrons to visualize and object of study rather than light waves as in standard optical microscopy. They differ from the transmission electron microscope in that instead of electrons passing through the specimen and then striking a phosphor screen to produce an image, the electrons strike the specimen under investigation and cause a secondary electron emission. This secondary electron emission forms the basis for a high resolution video display of the specimen. To aid in the development of the secondary electron emission specimens usually have a metal or carbon coating vapor deposited on their surfaces prior to being studied in the scanning electron microscope.

The striking "three dimensional" visual effects observed make this form of microscopy of special interest to the lift scientist. Great insight into in vivo structure can be obtained. In order to take full advantage of scanning electron microscopy high quality methods for preserving specimen morphology have been devised, such as the technique called "Critical Point Drying". In critical point drying specimens for study are first subjected to a graded series of drying solvents such as alcohol/water or acetone/water, finally progressing to 100% alcohol or acetone. The alcohol or acetone is then usually replaced with amyl acetate, and the amyl acetate saturated specimens are placed within the critical point dryer.

At this point a transitional fluid such as liquid carbon dioxide, nitrous oxide, or trifluorochloromethane is slowly fed into the critical point dryer to displace the amyl acetate. The pressure sealed dryer is then heated to bring the apparatus to the critical temperature and pressure. The now gaseous transitional fluid surrounds the specimen and may be bled off without surface tension distortion of the specimen's surface. The dried specimen is removed from the critical point dryer, vacuum coated with a metal or carbon, and may now be studied in the scanning electron microscope.

I have discovered that specimen preservation results directly comparable or even superior to critical point drying may be obtained in a greatly simplified manner. In my method alcohol or acetone dried specimens are placed in a fluorocarbon transitional fluid, the fluorocarbon liquid is frozen, and then vacuum sublimated, leaving a dry specimen of equivalent or superior quality morphological preservation to that obtained with critical point drying, but without the necessity for costly critical point drying instrumentation and the time consuming procedures required.

Accordingly it is an object of this invention to provide a simple method for drying specimens to be examined in the scanning electron microscope.

Another object is to reduce equipment requirements for scanning electron microscope sample preparation.

Another object is to provide a rapid method for preparing quantities of specimens for scanning electron microscope observation.

A further object is to provide efficient, selective specimen lipid removal in a relatively inert environment.

SUMMARY OF THE INVENTION

The above and related objects have been obtained with the instant invention in which a select group of fluorocarbon solvents are employed to prevent surface tension specimen distortions, while at the same time providing selective lipid removal from specimen surfaces for clearer visualization under the scanning electron microscope.

Certain fluorocarbon solvents, especially several of those commonly referred to as "Freons", are known to be excellent selective solvents for lipids. (Freon is a registered trademark of E. I. Du Pont De Nemours & Co., Inc.). In addition they are characterized by high density and low surface tension, together with extremely high chemical stability. These compounds are known primarily for their refrigeration characteristics.

In my method I first remove water from the specimen to be studied by placing it in a graded series of either ethyl alcohol/water or acetone/water, ending in either 100% alcohol or 100% acetone. The solvent saturate specimen is then placed in either a 1:1 mixture of fluorocarbon solvent and alcohol, or a 1:1 mixture of fluorocarbon solvent and acetone. Finally the specimen is placed in pure fluorocarbon liquid solvent for a period of time. The fluorocarbon solvent is now frozen and sublimated away under vacuum, leaving behind a topologically well preserved specimen suitable for vacuum coating and scanning electron microscope observation.

I have found two fluorocarbon solvents especially well suited for this procedure. They are 1,1-difluorotetrachloroethane, and 1,2-difluorotetrachloroethane. Both are solid at room temperature, and have a boiling point of approximately 93° C. Either solvent is melted at only slightly above room temperature, so that specimens are subjected to extremely mild temperature conditions within a virtually inert transitional fluid. Solvent freezing may be accomplished by simply allowing these solvents to solidify at room temperature. Sublimation of these solvents can be accomplished rapidly. For example, a one gram sample of 1,1-difluorotetrachloroethane, placed in a vacuum tight jar and evacuated by a 25 liter/minute-two stage rotary vacuum pump, is sublimited completely within fifteen minutes. The excellent refrigerant characteristics of either solvent (approximately 37 calories per gram) enable these solvents to remain rigidly solid during sublimation, thus maintaining the structural integrity of the specimen during this transitional liquid removal procedure.

Another fluorocarbon solvent which may be used for this procedure is trifluorotrichloroethane, which has a freezing point of approximately −35° C., and a boiling point of approximately 48° C. In this case cooling is required to maintain the solvent in a liquid condition while it is acting as a transitional fluid, and a refrigerated platen is required to keep the solvent solidly frozen during sublimation.

Typical examples of my invention are as follows:

EXAMPLE 1

Chunks of Tracheal Epithelium from the Dog

Fixation Procedure:
Primary fixation:
Phosphate buffered glutaraldehyde (1 hour at room temperature).

Post-fixation:
Phosphate buffered osmium tetroxide (1 hour at room temperature).
Dehydration:
1. Graded series of acetone to 100%.
2. 1:1 mixture of acetone-1,1-difluorotetrachloroethane (1 hour at 40° C.).
Infiltration:
Incubation for 30, 60, or 90 minutes in 1,1-difluorotetrachloroethane at 60° C.
Solidification (freezing) at room temperature.
Drying:
Once specimens were frozen in the fluorocarbon solvent they were pumped briefly with a mechanical forepump and then placed in a dessicator and pumped overnight on house vacuum. Samples were then mounted on studs and coated in a vacuum evaporator with 100 Å of gold:palladium. Results:
Tissue has been preserved with normal characteristics comparable to results obtained with critical point drying.

EXAMPLE 2

Cultured Dog Tracheal Epithelial Out-Growths

Fixation Procedure:
Primary fixation:
Phosphate buffered glutaraldehyde (1 hour at room temperature).
Post-fixation:
Phosphate buffered osmium tetroxide (1 hour at room temperature).
Dehydration:
1. Graded series of alcohol to 100%.
2. 1:1 mixture of alcohol:1,1-difluorotetrachloroethane (10 minutes at 40° C.).
Infiltration:
Incubation for 5 minutes in 1,1-difluorotetrachloroethane at 60° C.
Solidification (freezing) at room temperature.
Drying:
Once solidified in fluorocarbon solvent samples were pumped briefly with a mechanical forepump and then placed in a dessicator and pumped overnight on house vacuum. Samples were than mounted on studs and coated in a vacuum evaporator with 100 Å of gold:palladium.
Results:
Tissue has been preserved with normal characteristics comparable to results obtained with critical point drying.

While the best mode for using my invention has been disclosed in detail, various modifications and improvements will occur to those skilled in the art. Accordingly the spirit and scope of the present invention is to be limited only by the following claims.

I claim:
1. A method for preparing a biological specimen for examination in the scanning electron microscope, which comprises the steps of:
   (A) Drying said specimen in a graded series of a drying solvent;
   (B) Replacing said drying solvent within said specimen by immersing said specimen in a melted fluorocarbon solvent selected from the group consisting of
   1,1-difluorotetrachloroethane and
   1,2-difluorotetrachloroethane;
   (C) Solidifying said melted fluorocarbon solvent and specimen at room temperature; and
   (D) Vacuum sublimating said solidified fluorocarbon solvent from said specimen.
2. A method according to claim 1 in which said fluorocarbon solvent is 1,1-difluorotetrachloroethane.
3. A method according to claim 1 in which said fluorocarbon solvent is 1,2-difluorotetrachloroethane.
4. A method according to claim 1 in which said drying solvent is alcohol.
5. A method according to claim 1 in which said drying solvent is acetone.

* * * * *